United States Patent
Furuta et al.

(10) Patent No.: US 6,666,030 B2
(45) Date of Patent: Dec. 23, 2003

(54) ICE COMPOSITION CONTAINING HYDROGEN PEROXIDE AND METHOD OF STORING PERISHABLE FOOD

(75) Inventors: Tsuneto Furuta, Fujisawa (JP);
Yoshinori Nishiki, Fujisawa (JP);
Masao Sekimoto, Yamato (JP);
Shyuhei Wakita, Fujisawa (JP)

(73) Assignee: Permelec Electrode Ltd., Kanagawa (JP)

( * ) Notice: Subject to any disclaimer, the term of this patent is extended or adjusted under 35 U.S.C. 154(b) by 0 days.

(21) Appl. No.: 10/155,961

(22) Filed: May 29, 2002

(65) Prior Publication Data

US 2002/0194852 A1 Dec. 26, 2002

(30) Foreign Application Priority Data

May 30, 2001 (JP) ............................. P.2001-162028
Aug. 1, 2001 (JP) ............................. P.2001-233381

(51) Int. Cl.[7] ................................................ F25C 21/00
(52) U.S. Cl. ............................................................. 62/1
(58) Field of Search ............................ 62/1, 59, 66, 340; 426/524

(56) References Cited

U.S. PATENT DOCUMENTS

| | | | | |
|---|---|---|---|---|
| 3,884,777 A | * | 5/1975 | Harke et al. | 205/472 |
| 3,884,778 A | * | 5/1975 | Eng et al. | 205/471 |
| 3,889,689 A | * | 6/1975 | Rosen | 131/293 |
| 3,927,189 A | * | 12/1975 | Jayawant | 423/513 |
| 4,347,232 A | * | 8/1982 | Michaelson | 423/584 |
| 4,801,407 A | * | 1/1989 | Hignett et al. | 252/186.1 |
| 5,081,068 A | * | 1/1992 | Endo et al. | 134/2 |
| 5,082,647 A | * | 1/1992 | Chuang | 423/584 |
| 5,338,531 A | * | 8/1994 | Chuang et al. | 423/584 |
| 5,708,119 A | * | 1/1998 | Deisenroth et al. | 528/70 |
| 5,747,078 A | * | 5/1998 | De Jong et al. | 426/9 |
| 5,846,898 A | * | 12/1998 | Chuang et al. | 502/181 |
| 5,858,430 A | * | 1/1999 | Endico | 426/241 |
| 5,925,588 A | * | 7/1999 | Chuang et al. | 502/181 |
| 6,013,297 A | * | 1/2000 | Endico | 426/335 |
| 6,045,684 A | * | 4/2000 | Wakita et al. | 204/265 |
| 6,063,279 A | * | 5/2000 | Yamasaki et al. | 210/605 |
| 6,113,773 A | * | 9/2000 | Shimamune et al. | 205/466 |
| 6,159,349 A | * | 12/2000 | Wakita et al. | 204/258 |
| 6,254,762 B1 | * | 7/2001 | Uno et al. | 205/466 |

FOREIGN PATENT DOCUMENTS

| | | | | |
|---|---|---|---|---|
| JP | 402290482 A | * | 11/1990 | ............... 62/66 |
| JP | 403049224 A | * | 3/1991 | |
| JP | 411350178 A | * | 12/1999 | ......... C25B/1/30 |

* cited by examiner

*Primary Examiner*—William E. Tapolcai
*Assistant Examiner*—Mohammad M. Ali
(74) *Attorney, Agent, or Firm*—Sughrue Mion, PLLC

(57) ABSTRACT

An ice composition obtained by freezing a liquid containing, dissolved therein, hydrogen peroxide produced by electrolysis; and a method of food storage using the composition. Hydrogen peroxide has a lower rate of dissipation into the air and better suitability for long-term storage than ozone. Furthermore, since hydrogen peroxide is electrolytically produced, it eliminates the trouble of transportation, storage, and dissolution. When seawater is used as a feed water for electrolysis, the ice composition thus obtained has a higher cooling effect because it has a melting point lower than 0° C.

5 Claims, 1 Drawing Sheet

ICE COMPOSITION CONTAINING HYDROGEN PEROXIDE AND METHOD OF STORING PERISHABLE FOOD

FIELD OF THE INVENTION

The present invention relates to an ice composition excellent in freezing ability and bactericidal activity. The invention further relates to a method of storing a perishable food, e.g., a fresh fish, vegetable, or fruit, with the ice composition.

DESCRIPTION OF THE RELATED ART

Cooling with ice is generally known as an effective technique for food storage. In cooling with ice, the temperature of the food is lowered to about 0 to 5° C. and the putrefying and other bacteria adherent to or contained in the food are inhibited from propagating. However, this technique is frequently insufficient for fully inhibiting putrefaction and attaining freshness preservation and is hence unsuitable for long-term storage.

Under these circumstances, an ozonized ice obtained by dissolving ozone in water and freezing the ozonized water has been proposed as a material for perishable food storage which is more effective than the storage based only on the cooling power of ice (see Japanese Patent Laid-Open Nos. 131865/1989 and 294911/1999). Ozonized water is generally produced by a method in which ozone generated by electric discharge in air or oxygen or by water electrolysis with a solid electrolyte is dissolved in water.

However, in such ozonized water, most of the ozone is dispersed as fine bubbles in the water and dissipates into the air in a short period of time. Because the ozone concentration thus decreases, there is a problem that a sufficient effect of freshness preservation and a sufficient bactericidal effect do not last. Furthermore, use of an ozonized ice has the following drawbacks. Since an ozonized ice generates ozone while melting, the bactericidal effect of ozone long continues when the initial ozone concentration is high. Virtually, however, there is a problem that even when high-concentration ozonized water is frozen, the ozone concentration decreases considerably during the freezing step. It is therefore necessary to conduct preliminary cooling, quick freezing, or the like for actually producing a high-concentration ozonized ice capable of retaining bactericidal activity and freshness-preserving properties over a long period of time. At present, investigations are being made on processes for producing the ice. Although various apparatus have been proposed based on the investigations, they have complicated structures and this is an obstacle to practical use thereof. Furthermore, since ozone is sparingly soluble in water, it is difficult to produce high-concentration ozonized water and this constitutes an obstacle to the production of the ozonized ice.

Besides ozone, which has such drawbacks, hydrogen peroxide is known as a compound having bactericidal activity. It has been proposed to eject particles of an ice containing hydrogen peroxide onto a semiconductor to clean it (see Japanese Patent Laid-Open No. 49224/1991).

In this method of cleaning, not only the ice particles ejected physically remove impurity particles, fouling substances, etc., from the surface of the semiconductor substrate, but also impurities which cannot be physically removed are removed by the chemical action of hydrogen peroxide to further conduct surface modification. In this cleaning method, since hydrogen peroxide is produced by the discharge method, impurities are apt to come into the hydrogen peroxide. This ice hence has a drawback that it is less suitable for application to foods. Namely, the ice containing hydrogen peroxide (ice composition) disclosed in that reference is intended only for use in cleaning, and there is no description therein concerning the storage of foods.

SUMMARY OF THE INVENTION

The present invention has been made in view of the drawbacks of the related-art techniques described above.

Accordingly, one object of the present invention is to provide an ice composition suitable for use in the storage of perishable foods.

Another object of the present invention is to provide a method of storing a perishable food with the ice composition.

According to one embodiment of the invention, an ice composition containing hydrogen peroxide is provided, the composition being obtained by freezing an aqueous hydrogen peroxide solution prepared by electrolyzing water.

According to another embodiment of the invention, a method of perishable food storage is provided which comprises adding an ice composition containing hydrogen peroxide to a perishable food and storing the perishable food with the aid of the bactericidal activity of the hydrogen peroxide and the freezing ability of the ice composition.

BRIEF DESCRIPTION OF THE DRAWING

The foregoing and other aims and advantages of the invention will be apparent from the following detailed description and the accompanying drawing, in which:

The FIGURE is a graph showing the relationship between the lapse of time and the hydrogen peroxide concentration in a pseudo-seawater in Example 3.

DETAILED DESCRIPTION OF THE INVENTION

Figure 1:
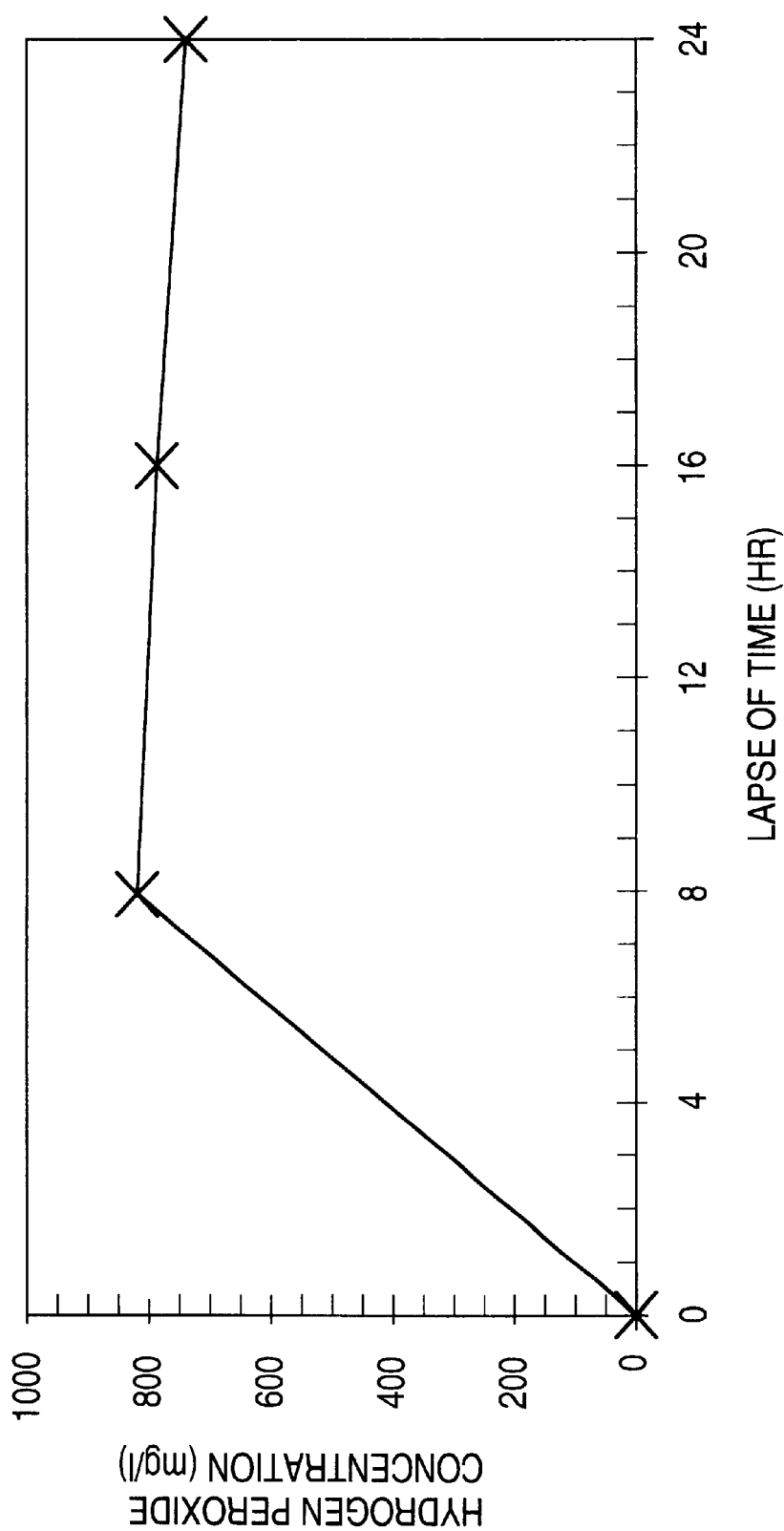

A feature of the ice composition of the invention resides in that the hydrogen peroxide contained in the ice composition is prepared by an electrolytic process. This ice composition is preferably used for the storage of perishable foods.

The hydrogen peroxide-containing ice composition according to the related-art technique described above is obtained from a solution prepared by dissolving hydrogen peroxide gas obtained by the discharge method in water. Consequently, impurities attributable to the discharge are apt to come into the hydrogen peroxide gas. In addition, the preparation of the composition necessitates the step of dissolving the hydrogen peroxide gas in water.

In contrast, in the ice composition of the invention, the hydrogen peroxide contained therein is obtained by an electrolytic process. Since on-site production of hydrogen peroxide is hence possible, not only the trouble of transporting, storing, and adding hydrogen peroxide as a chemical is avoided but also the step of dissolving hydrogen peroxide gas, which is relatively poorly water-soluble, in water is unnecessary. Moreover, since there is little impurity inclusion, a hydrogen peroxide-containing ice composition having a relatively high purity is obtained.

The related-art technique concerning a hydrogen peroxide-containing ice composition is not based on the idea that the cooling power of ice is utilized, and this ice composition is not used for the storage of perishable foods as stated above.

The hydrogen peroxide-containing ice composition of the invention is useful for the storage of foods. In particular, marine products such as fresh fish are thought to neither freeze nor change in quality at temperatures of from −1 to −2° C. Namely, it is known that storage at a temperature of 0° C., which is the ice point, or at a slightly lower temperature is effective in long-term freshness preservation. In the case where ice obtained by freezing fresh water is used for food storage by immersing the food in the ice, the temperature of the food during the storage is kept at about 0 to 2° C. at the lowest. In general, for the storage of marine products such as fresh fish for which a temperature of from −1 to −2° C. is effective, ice and seawater are used in combination for realizing this lower temperature.

In the case of using the hydrogen peroxide-containing ice composition of the invention also, a bactericidal activity and a temperature of from −1 to −2° C., which is suitable for the storage of fresh fish and the like, can be simultaneously realized by using the ice composition in combination with seawater. Furthermore, use of seawater, which is water containing metal ions, as a feed material for the hydrogen peroxide-containing ice is advantageous in that the freezing point lowers due to the sodium chloride contained therein and storage at −1 to −2° C. is hence possible. In particular, use of this ice, which is composed of almost the same components as seawater, as a cooling material eliminates adverse influences on the marine products and is hence more effective from the standpoint of quality preservation.

When the hydrogen peroxide-containing ice composition of the invention is used for storing a food, not only the freshness of the food is preserved due to the cooling action of the ice but also hydrogen peroxide acts on the food to sterilize it. In the case where the hydrogen peroxide contained in the ice composition is in contact with the food, direct sterilization occurs. In other cases, the hydrogen peroxide originally contained in inner parts of the ice composition is present in the water resulting from melting and this hydrogen peroxide comes into contact with the food to sterilize it.

In actual cold storage of foods, the ice composition of the invention is used in the same manner as in storage with ice heretofore in use. Namely, the ice composition is packed into a container together with a perishable food, e.g., a fishery product. In the container, the perishable food is in contact with the surface of the ice and kept cooled at a nearly constant temperature around the freezing point. The perishable food simultaneously comes into direct contact with the hydrogen peroxide present on the surface of the ice composition or into contact with the hydrogen peroxide solution resulting from melting. Thus, the putrefying and other bacteria adherent to the perishable food are destroyed or inhibited from propagating, whereby the food can be kept fresh over a long period of time. In addition, since the ice composition used for cooling is maintained at a temperature around the freezing point as stated above, hydrogen peroxide is gradually supplied to the perishable food through melting and does not dissipate in a short time period. Consequently, it is possible to store foods over a longer time period. When the ice composition of the invention is used for food storage in combination with water or seawater, the rate of supplying hydrogen peroxide (melting rate of the ice composition) can be regulated.

Besides being used for storing perishable foods, etc., the ice composition of the invention can be kept in a frozen solid state. Consequently, the hydrogen peroxide contained in the ice composition can be easily transported to a desired place unlike gaseous hydrogen peroxide. The composition can hence be suitable for use, e.g., in places where water intake is difficult or on the sea.

The hydrogen peroxide contained in the ice composition of the invention is one produced by electrolysis. An aqueous hydrogen peroxide solution having an appropriate concentration can be obtained by regulating the amount of feed water and the current efficiency or by directly measuring the hydrogen peroxide concentration of the electrolytic liquid during electrolysis. The preferred range of the hydrogen peroxide concentration in the ice composition to be used for food storage is from 20 to 500 ppm. In case the where the hydrogen peroxide concentration is lower than the lower limit, sufficient bactericidal effect is not obtained. In case the where the hydrogen peroxide concentration exceeds the upper limit, the bactericidal activity is excessively high and problems arise such as hydrogen peroxide remaining in the food and food deterioration.

Hydrogen peroxide is generated by the following electrode reactions.

Anode reaction: $H_2O \rightarrow \frac{1}{2}O_2 + 2H^+ + 2e^-$

Cathode reaction: $H_2O + O_2 + 2e^- \rightarrow HO_2^- + OH^-$

When fresh water is used as a feed material, a liquid containing, dissolved therein, hydrogen peroxide as substantially the only solute is obtained by electrolysis. When seawater is used, seawater containing hydrogen peroxide dissolved therein is obtained.

In the case where municipal water such as tap water is used as a feed water, the hardness-elevating ingredients are preferably removed beforehand from the municipal water with an ion-exchange resin or the like. It is desirable to use a feed water containing an electrolyte, e.g., sodium chloride, because it contributes to a reduction in electrolytic voltage and is hence economically advantageous. The electrolyte concentration in this case need not be as high as that in seawater.

Electrolytic cells usable for producing hydrogen peroxide are not particularly limited. For example, the following electrolytic cell and constituent members can be used.

Although ordinary oxygen-generating anodes and hydrogen-generating cathodes may be used, it is especially preferred to use an oxygen gas electrode as the cathode. The oxygen gas electrode preferably employs a metal such as gold, a metal oxide, or a carbon such as graphite or conductive diamond as a catalyst. The electrode may be one having a surface coating made of an organic material such as polyaniline or a thiol. These catalysts may be used alone in a platy or porous form or may be deposited on a substrate, e.g., a plate, metal gauze, powder sinter, or metal fiber sinter, made of a corrosion-resistant material such as, e.g., stainless steel, zirconium, silver, or carbon by a pyrolytic method, adhesion with a resin, composite plating, etc.

The electricity feeder for the cathode can be a carbon, a metal such as, e.g., nickel or titanium, or an alloy or oxide thereof. Such a feeder is preferably used in a porous or sheet form. For the purpose of smoothly supplying feed water and smoothly discharging the gases generated by the reactions and the water which has undergone electrolysis, it is desirable to scatteringly deposit a hydrophobic or hydrophilic material on the feeder surface. Formation of a hydrophobic sheet on the cathode on a side opposite to the anode is effective in controlling gas supply to the reaction surface. In case the where the conductivity of the catholyte is low, the cell voltage is increased or the electrode life is shortened. In this case, it is desirable to employ a structure in which the cathode is united with an ion-exchange membrane for the purpose of preventing pollution by the gas electrode material and for other purposes.

The amount of oxygen to be fed to the cathode is preferably about from 1 to 2 times the theoretical amount. The oxygen source may be air or a commercial oxygen cylinder. Alternatively, the oxygen generated by water electrolysis in an electrolytic cell separately installed or the oxygen obtained from air through concentration with a PSA apparatus may be used. In general, the higher the oxygen concentration, the higher the current density at which hydrogen peroxide can be produced.

When a diaphragm is used for partitioning the electrolytic cell into an anode chamber and a cathode chamber, the hydrogen peroxide obtained by the electrode reactions can be held stably without coming into contact with the counter electrode. Furthermore, even when the water to be electrolyzed has a low conductivity, the diaphragm functions to enable electrolysis to proceed speedily. Moreover, when seawater is used, the generation of hypochlorous acid and the decomposition of hydrogen peroxide by the hypochlorous acid generated can be prevented.

The diaphragm can be a neutral diaphragm or an ion-exchange membrane. Especially for the purpose of preventing the oxidation of chloride ions on the anode, the use of a cation-exchange membrane is preferred. Examples of the diaphragm material include fluororesins and hydrocarbons. From the standpoint of corrosion resistance, the former is preferred.

Examples of anode catalysts capable of stable use include noble metals such as iridium, platinum, and ruthenium, oxides of these noble metals, and mixed oxides containing an oxide of a valve metal such as titanium or tantalum. Also, carbons such as graphite and conductive diamond can be used. In the case of using a feed water containing chloride ions, such as, e.g., seawater, it is desirable to select a catalyst so that the oxygen-yielding reaction which is a water oxidation reaction occurs preferentially to the generation of chlorine gas or hypochlorous acid by chloride ion oxidation. Manganese dioxide and mixed oxides such as manganese-vanadium, manganese-molybdenum, and manganese-tungsten oxides are known to inhibit the discharge of chloride ions (generation of chlorine gas). Such an anode catalyst can be deposited on the surface of an electrode base, e.g., titanium, by a method comprising immersing the base in an aqueous solution containing, dissolved therein, ions of the components of the catalyst.

The material of the electrolytic cell is preferably a glass-lined material, carbon, highly corrosion-resistant material such as titanium or stainless steel, PTFE resin, or the like from the standpoints of durability and hydrogen peroxide stability.

Preferred electrolysis conditions include a liquid temperature of from 5 to 60° C. and a current density of from 0.1 to 100 A/dm$^2$. Although the distance between the electrodes should be small so as to reduce the resistance loss, it is preferably from 1 to 50 mm from the standpoints of reducing the pressure loss for the pump for feeding water to be electrolyzed and for maintaining an even pressure distribution.

As stated hereinabove, seawater can be advantageously used in the invention. However, seawater contains organic compounds and halide ions dissolved therein. The total organic carbon (TOC) amount in seawater is about 10 ppm although it varies depending on location. When seawater having a TOC of about 10 ppm is electrolyzed, the chlorine gas or hypochlorous acid generated by the oxidation of chloride ions chlorinates the organic compounds to yield a tetrahalomethane (THM) and the like. Since inclusion of an organic halogen compound into the ice composition to be used for food storage is fatal, it is desirable to remove organic compounds serving as starting materials for organic halogen compounds before the initiation of electrolysis.

Examples of techniques for removing organic compounds dissolved in seawater include: a method in which the organic compounds are mechanically separated with a strainer; a method in which flocs and other suspended matters in the seawater are coagulated with a coagulant and then separated; a method in which the seawater is treated with activated carbon to adsorb the organic compounds onto the activated carbon and thereby remove them from the seawater; and a method in which the organic compounds are decomposed by ultraviolet irradiation or addition of ozone or hydrogen peroxide. These methods may be used alone or in combination of two or more thereof.

By performing those treatments, the content of residual organic compounds in the seawater can be reduced to 0.1 to 1.0 ppm.

Subsequently, the seawater thus treated may be passed through a column packed with activated carbon to thereby adsorptively remove low-molecular organic compounds remaining in the seawater. Thus, the content of organic compounds can be reduced to the order of 0.1 ppm. A zeolite or activated alumina may be used for the adsorptive removal in place of activated carbon.

As the electrolysis of seawater is continued, the hydroxides or carbonates of calcium and magnesium gradually deposit on the cathode surface. It is preferred to periodically conduct cleaning with hydrochloric acid for removing these deposits.

The liquid thus obtained through electrolysis is sent to an ice-making machine immediately or after having been stored in a tank for a while, and is frozen to thereby obtain an ice composition containing hydrogen peroxide. It is possible to use a method which comprises electrolytically generating hydrogen peroxide in a concentration higher than that necessary for an ice composition, diluting this hydrogen peroxide solution with tap water or seawater, and then obtaining a hydrogen peroxide-containing ice composition therefrom.

For freezing the hydrogen peroxide solution (obtained from a feed water other than seawater), an ice-making machine heretofore in general use may be used. Since the amount of hydrogen peroxide which decomposes during freezing is only slight, no special operation is required.

In the case of a hydrogen peroxide solution produced from seawater as a feed water, it is desirable to conduct preliminary cooling or to conduct quick freezing with a liquid coolant because seawater is generally difficult to freeze.

The invention will be explained below by reference to the following Examples, which relate to the production of a hydrogen peroxide-containing ice composition according to the invention. However, the invention should not be construed as being limited by these Examples.

EXAMPLE 1

A soft water from which hardness-elevating ingredients had been removed was supplied as feed water to an electrolytic hydrogen peroxide generator to obtain a soft water containing hydrogen peroxide in a concentration of 1,500 mg/l. A 100 ml portion of the soft water thus obtained was placed in a polypropylene vessel and frozen in a freezer. After 7 days, the resulting ice was thawed and examined for hydrogen peroxide concentration. As a result, the residual hydrogen peroxide concentration was found to be 1,420 mg/l and the degree of remaining hydrogen peroxide was 95%. It was found that this ice composition containing hydrogen peroxide enables long-term storage of foods. The hydrogen peroxide-containing ice composition had the same appearance as ices not containing hydrogen peroxide.

EXAMPLE 2

Seawater was directly supplied as a feed water to an electrolytic cell to obtain a seawater containing hydrogen peroxide in a concentration of 5,200 mg/l. This seawater was diluted with additional seawater to a hydrogen peroxide concentration of 500 mg/l. A 100 ml portion of this water was placed in a polypropylene vessel and quickly frozen. After 3 days, the resulting ice was thawed and examined for the concentration of residual hydrogen peroxide. As a result, the residual hydrogen peroxide concentration was found to be 490 mg/l and the degree of remaining hydrogen peroxide was 98%.

COMPARATIVE EXAMPLE 1

Ozone was dissolved in tap water to prepare ozonized water having a concentration of 10 mg/l. This ozonized water was placed in a polypropylene vessel and frozen in a freezer. After 7 days, the resultant ice was thawed and examined for the concentration of residual ozone. As a result, the residual ozone concentration was found to be 0.3 mg/l and the degree of remaining ozone was 3%. This ice was inferior in degree of remaining ozone to the hydrogen peroxide-containing ice compositions.

EXAMPLE 3

1 kg of the hydrogen peroxide-containing ice composition produced in Example 1 and 1 liter of a 3 wt % aqueous sodium chloride solution as a pseudo-seawater were placed in a container made of a styrene resin foam. The resulting mixture was stored in a room at a temperature of 25° C. for 24 hours to determine the relationship between the lapse of time and the hydrogen peroxide concentration in the pseudo-seawater. The results obtained are shown by the graph of the accompanying FIGURE.

It was found that the hydrogen peroxide concentration in the pseudo-seawater could be maintained almost constant over a long period of time as shown in the FIGURE. It is expected from these results that an appropriate constant hydrogen peroxide concentration can be maintained over a long period of time by regulating the hydrogen peroxide concentration in the ice composition and changing the proportion of the hydrogen peroxide-containing ice composition to the seawater or the like.

EXAMPLE 4

The aqueous hydrogen peroxide solutions obtained by the methods described in Examples 1 and 2 were diluted with municipal water to adjust the hydrogen peroxide concentration to 100 mg/l. Each of the diluted aqueous hydrogen peroxide solutions was placed in a polyethylene vessel and frozen in a freezer. The frozen water containing hydrogen peroxide and a cotton cloth (5×5 cm) which had undergone high-pressure steam sterilization (121° C., 15 minutes) and then dropping of a liquid containing *Escherichia coli* (number of cells: $10^6$–$10^7$/ml) thereon were placed in a container made of a styrene foam. The container was stored in a thermostatic chamber (5° C.) for 24 hours. After the 24 hours storage, the cotton cloth was taken out of the container and rinsed with 20 ml of an SCDLP culture medium (SCDLP medium manufactured by Nihon Seiyaku Co., Ltd. to which 0.1% sodium thiosulfate had been added). The resulting rinsing was examined for the number of viable cells by the pour plate culture method (35±1° C., 2 days) using an SA culture medium (standard agar medium manufactured by Eiken Chemical Co., Ltd.). As a Comparative Example, an ice obtained by freezing municipal water in a freezer was subjected to the same test.

The results obtained are shown in Table 1 below. As is apparent from Table 1, when the hydrogen peroxide-containing ice compositions prepared by diluting the aqueous hydrogen peroxide solutions obtained by the methods used in Examples 1 and 2 and freezing the diluted solutions were used for 24 hours storage, the number of cells of *Escherichia coli* was almost zero. It was found that these ice compositions had a far higher bactericidal effect than the ice of the Comparative Example obtained from municipal water.

TABLE 1

| | | Number of viable cells | |
|---|---|---|---|
| | Method of ice preparation | Initial | After 24 hrs |
| Example 4 | Stored with ice prepared by the method of Example 1 | $7.8 \times 10^6$ | Below detection limit |
| | Stored with ice prepared by the method of Example 2 | $7.8 \times 10^6$ | Below detection limit |
| Comparative Example | Stored with ice made from municipal water | $7.8 \times 10^6$ | $2.78 \times 10^4$ |

EXAMPLE 5

The aqueous hydrogen peroxide solutions obtained by the methods described in Examples 1 and 2 were diluted with municipal water in the same manner as in Example 4, to prepare 1 kg each of ices containing hydrogen peroxide in a concentration of 100 mg/l. Each ice was packed into a container made of a styrene resin foam together with 1 kg of fresh saurels. A lid was placed on each container. The fish were stores in the closed state for 24 hours. The degree of propagation of various bacteria adherent to the fish was determined in the following manner. Standard agar media (manufactured by Eiken Chemical Co., Ltd.) for general various bacteria were respectively pressed against the body of a fish before the storage and the body of a fish after the storage. The media were then placed in a thermostatic chamber (35–37° C.) to incubate for 48 hours. Thereafter, the area of the colony which had grown on each medium was measured, and these two media were compared in the colony area.

The results obtained are shown in Table 2 below. As shown in Table 2, the area of the colony grown on the medium in the case of the 24 hours storage with each hydrogen peroxide-containing ice was from 1/18 to 1/10 the colony area for the fish before the storage. In contrast, the colony area for the fish stored with the ice made from municipal water was 2.6 times the colony area for the fish before the storage.

TABLE 2

|  | Method of ice preparation | Area of colony Initial | After 24 hrs |
|---|---|---|---|
| Example 5 | Stored with ice prepared by the method of Example 1 | 79 mm² | 8 mm² |
|  | Stored with ice prepared by the method of Example 2 | 89 mm² | 5 mm² |
| Comparative Example | Stored with ice made from municipal water | 77 mm² | 200 mm² |

The ice composition containing hydrogen peroxide of the invention is characterized as being obtained by freezing an aqueous hydrogen peroxide solution prepared by hydrolyzing water.

Since the hydrogen peroxide contained in the ice composition of the invention is produced by electrolysis, on-site production of hydrogen peroxide is possible. Consequently, not only the trouble of transporting, storing, and adding hydrogen peroxide as a chemical is avoided, but also a gas dissolution step is unnecessary.

Hydrogen peroxide does not rapidly dissipate during freezing or storage unlike ozone or the like, and is gradually supplied to perishable foods, etc. Consequently, the foods can be stored over a longer period of time.

Use of this ice in combination with seawater is effective especially from the standpoint of preserving the quality of marine products.

The ice composition of the invention may be produced through the electrolysis of a water containing metal ions, e.g., seawater. The use of seawater brings about an improved cooling effect. Namely, the ice composition obtained by freezing seawater has a temperature lower than 0° C., so that foods can be stored at a more effective temperature of below the ice point. Furthermore, in the case of marine products, use of this ice, which is composed of almost the same components as seawater, for cooling eliminates adverse influences on the marine products and is hence more effective from the standpoint of quality preservation.

The method of perishable food storage of the invention comprises adding an ice composition containing hydrogen peroxide to a perishable food and storing the perishable food with the aid of the bactericidal activity of the hydrogen peroxide and the freezing ability of the ice composition.

Unlike the related-art technique in which foods are stored based on a bactericidal activity alone or a cooling power alone, the method of the invention is characterized in that a food is stored with the ice composition which combines the bactericidal activity of hydrogen peroxide and the cooling power of ice. Consequently, the food can be stored more efficiently over a longer time period.

Furthermore, as compared with the ozone in ozonized ice compositions, the hydrogen peroxide contained in the ice composition used in the method of the invention has a lower decomposition or dissipation rate. Consequently, the effectiveness of storage lasts over a long period of time. In the case where the ice composition has too low a melting rate, or where the rate of hydrogen peroxide supply to the food is too low, the bactericidal efficiency can be heightened by using the ice composition in combination with water.

It should further be apparent to those skilled in the art that various changes in form and detail of the invention as shown and described above may be made. It is intended that such changes be included within the spirit and scope of the claims appended hereto.

This application is based on Japanese Patent Application No. 2001-162028 filed May 30, 2001 and Japanese Patent Application No. 2001-233381 filed Aug. 1, 2001, the disclosures of which are incorporated herein by reference in their entirety.

What is claimed is:

1. An ice composition containing hydrogen peroxide, the composition being obtained by freezing an aqueous hydrogen peroxide solution prepared by electrolyzing seawater, said ice composition have a hydrogen peroxide concentration of from 20 to 500 ppm.

2. The ice composition of claim 1, for use in the storage of a perishable food.

3. The ice composition of claim 1, having a melting point of below 0° C.

4. A method of perishable food storage which comprises providing an ice composition containing hydrogen peroxide in a concentration of from 20 to 50 ppm prepared by electrolyzing seawater, and storing a perishable food in the presence of the ice composition, said ice composition having bactericidal activity due to release of hydrogen peroxide and cooling ability.

5. The method of claim 4, wherein said ice composition has a melting point of below 0° C.

* * * * *